United States Patent [19]

Uchiyama

[11] Patent Number: 4,483,956

[45] Date of Patent: Nov. 20, 1984

[54] ACRYLIC RESIN ARTICLE

[75] Inventor: Hiroshi Uchiyama, Hirakata, Japan

[73] Assignees: E. C. Chemical Ind. Co., Ltd.; C. Itoh & Co., Ltd., both of Osaka, Japan

[21] Appl. No.: 486,546

[22] Filed: Apr. 19, 1983

[30] Foreign Application Priority Data

Apr. 19, 1982 [JP] Japan .................................. 57-63958

[51] Int. Cl.³ ............................................... C08K 5/05
[52] U.S. Cl. .................................... 524/384; 524/533; 524/560
[58] Field of Search .......................... 524/384, 533, 560

[56] References Cited

U.S. PATENT DOCUMENTS 4,193,906 3/1980 Hatanaka ............................. 524/384

FOREIGN PATENT DOCUMENTS 116889 8/1943 United Kingdom ................ 524/384

Primary Examiner—Joseph L. Schofer
Assistant Examiner—T. M. Reddick
Attorney, Agent, or Firm—Wenderoth, Lind & Ponack

[57] ABSTRACT

An acrylic resin article comprising a methyl methacrylate polymer and dibenzylidene sorbitol or its derivative as essential ingredients; and a process for producing an acrylic resin article, which comprises putting a composition comprising a methyl methacrylate monomer or a mixture of a methyl methacrylate polymer and a methyl methacrylate monomer and dibenzylidene sorbitol or its derivative in a mold, and thereafter polymerizing the methyl methacrylate monomer in the composition.

4 Claims, No Drawings

ACRYLIC RESIN ARTICLE

This invention relates to an acrylic resin article, particularly an acrylic resin denture, having improved resistance to shrinkage and soiling, and a process for producing it.

Molded articles of a methyl methacrylate polymer have excellent transparency and high hardness and find extensive applications as transparent doors and other building materials, electrical component parts, and a denture and other medical articles. These molded articles are obtained by such means as cast molding or injection molding.

In the production of these acrylic resin articles, shrinkage of the articles during molding has always been a problem. To improve resistance to soiling in these articles is also an important subject, and this is especially strongly desired in such uses as a denture which is susceptible to soiling.

Attempts have previously been made to reduce the shrinkage of acrylic resin articles by adding silica gel to the starting acrylic resins. But this results in decreased mechanical strength and reduced transparency, and cannot give satisfactory products.

It is an object of this invention therefore to overcome the aforesaid defects of the prior art, and to provide acrylic resin articles having resistance to shrinkage and soiling, and an acrylic resin composition capable of giving such products, and a process for producing such products.

The present invention is based on the discovery that a molded article prepared from an acrylic resin containing dibenzylidene sorbitol or its derivative has resistance to soiling and even when it is soiled, the soiling can be easily removed, and that this molded article has very high dimensional stability.

According to this invention, there is provided an acrylic resin article comprising a methyl methacrylate polymer and dibenzylidene sorbitol or its derivative as essential ingredients.

The acrylic resin article, as referred to in the present specification and claims, denotes a molded article prepared from a methyl methacrylate polymer, which is obtained, for example, by a cast molding method comprising casting a syrupy or slurry-like methyl methacrylate monomer or a syrupy or slurry-like mixture of a methyl methacrylate polymer and a methyl methacrylate monomer into a mold, and polymerizing and solidifying the methyl methacrylate monomer, or by a method comprising injection-molding a methyl methacrylate polymer.

Dibenzylidene sorbitol (hereinafter referred to as DBS) used in the present invention is a known compound obtained by the dehydrocondensation reaction of 1 mole of d-sorbitol with 2 moles of benzaldehyde. It is known as a gelling agent for organic liquids.

The derivative of dibenzylidene sorbitol denotes a product obtained by the dehydrocondensation reaction as in the production of DBS from benzaldehyde having at least one substituent such as alkyl groups, alkoxy groups, hydroxyl groups or halogen atoms on the aromatic ring and a sugar alcohol having a valence of 5 or more, for example a pentitol such as xylitol, arabitol or adonitol, or a hexitol such as sorbitol or mannitol. Compounds obtained by this reaction are described, for example, in Japanese Laid-Open patent publications Nos. 33558/1979 and 20378/1974.

The molded article of this invention contains 0.1 to 3% by weight, preferably 0.1 to 1.5% by weight, more preferably 0.3 to 1.5% by weight, of DBS or its salt based on the total weight of the methyl methacrylate polymer and DBS or its derivative.

The molded article of this invention can be produced by using a molding composition obtained by adding the aforesaid amount of DBS of its derivative to a methyl methacrylate monomer, a methyl methacrylate polymer or a mixture of a methyl methacrylate monomer and a methyl methacrylate polymer.

It is preferred to use a composition obtained by adding DBS or its derivative to the methyl methacrylate monomer or the methyl methacrylate monomer/polymer mixture. The composition may be put in a mold and polymerized under heat to give a final product. Surprisingly, it has been found that DBS in the composition promotes the polymerization of the methyl methacrylate monomer. Specifically, polymerization of the composition containing DBS can be completed within a given period of time at a lower temperature than a composition not containing DBS. The polymerization promoting effect of DBS is especially outstanding in the case of polymerization at low temperatures. For example, at a polymerization temperature of 65° C., the composition not containing DBS requires a period of 8 hours until its polymerization is completed, whereas the composition containing 0.7% of DBS requires only 5 hours.

The methyl methacrylate monomer or the methyl methacrylate monomer/polymer mixture containin DBS can be polymerized at a low temperature of, for example, 40° C. Usually, the polymerization comes to completion in 1 to 8 hours, preferably 0.5 to 5 hours, at a temperature of 40° to 100° C., preferably 60° to 100° C.

Any desired method can be used to include DBS or its derivative in the methyl methacrylate monomer or polymer. In the case of the polymer, the inclusion of DBS or its derivative may be effected by adding the aforesaid amount of DBS or its derivative to the monomer, heating the mixture to a temperature of 50° to 60° C. to form a solution, and then immediately polymerizing it; or by covering the surface of a powder of the polymer obtained by suspension polymerization with DBS or its derivative together with a wetting agent such as ethyl acrylate or dibutyl phthalate. In the case of the monomer, it may be effected by adding the aforesaid amount of DBS or its derivative to the monomer and heating the mixture to the aforesaid temperature to form a solution. When the methyl methacrylate monomer in which DBS or its derivative has been included as above is to be stored after cooling, the amount of DBS or its derivative is desirably 0.1% by weight or smaller. If DBS or its derivative is added in an amount exceeding this limit, weak gellation may occur upon cooling and the storage stability of the solution is likely to become poor. The methyl methacrylate monomer/polymer mixture containing DBS or its derivative can be easily prepared by mixing the methyl methacrylate monomer containing DBS or its derivative and the methyl methacrylate polymer containing DBS or its derivative which are obtained as above; or by partly polymerizing the monomer.

If the amount of DBS or its derivative in the molding composition obtained as above is less than 0.1% by weight, the shrinkage and soiling resistances of the acrylic resin article cannot be fully improved. If the amount of DBS or its derivative is larger than 0.7% by weight, the composition is likely to be gelled and become difficult to mix uniformly. However, by the aforesaid method involving covering the surface of the powdery methyl methacrylate polymer with DBS or its derivative together with a wetting agent, it is possible to prepare a composition containing more than 0.7% by weight of DBS or its derivative. The resulting composition containing a large proportion of DBS or its derivative can be used as a master batch.

In the present invention, the methyl methacrylate monomer or the methyl methacrylate monomer/polymer mixture is usually used after including therein a small amount of a peroxide polymerization catalyst such as benzoyl peroxide or methyl ethyl ketone peroxide.

The acrylic resin composition used for producing the acrylic resin article of this invention may contain a known coloring agent or an aggregate in amounts which do not adversely affect the improvement of shrinkage and soiling resistances. If a glass wool powder or silica gel is used as the aggregate, it serves to improve shrinkage resistance.

Molded articles, especially a denture, obtained by using the aforesaid acrylic resin composition have excellent dimensional stability (i.e. shrinkage resistance). Hence, false teeth can be firmly fixed. They are also resistant to soiling, and any soiling on the articles can be easily removed. In other words, they have high soiling resistance.

The following examples illustrate the present invention more specifically.

In these examples, the dimensional stability and soiling resistance of the acrylic resin articles were evaluated by the following methods.

(1) Dimensional stability

A plaster mold was made by using an outer brass mold in the form of an inverted truncated cone with the top surface circle having a diameter of 40 mm and the bottom surface circle having a diameter of 30 mm and an internal brass mold symmetrical in shape with the outer brass mold with the top surface circule having a diameter of 39 mm. A sample resin was cast into the plaster mold to produce a molded article in the shape of a bottomed, hollow, inverted truncated cone, 0.5 mm thick, with the top surface having an outside diameter of 40 mm, the bottom surface having an outside diameter of 30 mm was prepared, and taken out of the mold. When 24 hours elapsed after withdrawal from the mold, the inner brass mold used to mold the sample resin was fitted in the inside surface of the molded article, and the height (mm) of a protruding portion extending from the brass mold as a result of shrinkage of the molded article was measured. This height is defined as the amount of shrinkage.

(2) Soiling resistance

A black emulsion was prepared by mixing 5 parts by weight of carbon black, 5 parts by weight of castor oil and 90 parts by weight of water with vigorous stirring. A sample of a molded article was dipped in the emulsion, withdrawn 24 hours later, and washed with water. The color of the sample was then evaluated by visual observation.

EXAMPLE 1

(a) Ninety-five parts by weight of a powdery methyl methacrylate polymer (made by Nippon Synthetic Chemical Industry Co., Ltd.), 4 parts by weight of glyceryl monostearate and 1 part by weight of dibenzylidene sorbitol were mixed, and 200 parts by weight of hot water (50° to 60° C.) was added with stirring. The mixture was stirred for about 10 minutes and filtered by a centrifugal separator. The filtrate was washed with water and dried to give about 96 parts by weight of a mixture of the methyl methacrylate polymer and dibenzylidene sorbitol in which glyceryl monostearate was uniformly spread and adhered to the surface of the particles.

(b) The resulting mixture was gently put in 50 parts by weight of methyl methacrylate monomer containing 0.8 part by weight of methyl ethyl ketone peroxide as a catalyst, and after putting a closure over the mixture, it was left to stand at room temperature for 15 to 20 minutes. When the contents swelled to such a sticky state that upon touching by hand, the contents did not adhere to the hand. The contents were put in a mold for a denture, and polymerized at 100° C. for 30 to 40 minutes.

After the polymerization, the product was removed from the mold. The dimensional stability and soiling resistance of the denture were tested. The dimensional stability of the sticky resin mixture before placing in the mold was also tested.

The results are shown in Table 1.

COMPARATIVE EXAMPLE 1

A denture was produced in the same way as in Example 1 except that dibenzylidene sorbitol was not used. The dimensional stability and soiling resistance of the product were tested in the same way as in Example 1.

The results are shown in Table 1.

EXAMPLE 2

49.9 Parts by weight of methyl methacrylate monomer (made by Asahi Chemical Industry Co., Ltd.) and 0.1 part by weight of dibenzylidene sorbitol were put in a flask equipped with a reflux condenser, and heated to 60° to 70° C. to dissolve the dibenzylidene sorbitol. After allowing the solution to cool, it was transferred to a beaker.

One hundred parts by weight of the mixture prepared in (a) of Example 1 was gently added to the beaker, and a denture was produced in the same way as in Example 1, (b). The dimensional stability and soiling resistance of the product were tested in the same way as in Example 1, and the results are shown in Table 1.

EXAMPLE 3

A mixture was prepared in the same way as in Example 1, (a) except that 96 parts by weight of a powdery methyl methacrylate polymer (made by Mitsubishi Rayon Co., Ltd.), 3 parts by weight of sorbitan monoleate and 1 part by weight of (1,3)(2,4) p-methylbenzylidene sorbitol were used. A denture was produced in the same way as in Example 1, (b). The dimensional stability and soiling resistance of the product were tested in the same way as in Example 1. The results are shown in Table 1.

EXAMPLE 4

A mixture was prepared in the same way as in Example 1, (a) except that 97 parts by weight of a powdery methyl methacrylate polymer (made by Nippon Synthetic Chemical Industry Co., Ltd.), 2 parts by weight of sorbitan monolaurate (Nikkol SL-10, a product of Nikko Chemicals Co., Ltd.) and 1 part by weight of (1,3)(2,4)-benzylidene xylitol were used. Then, in the same way as in Example 1, (b), a denture was produced. In the same way as in Example 1, the dimensional stability and soiling resistance of the product were tested, and the results are shown in Table 1.

TABLE 1

| Run | Dimensional stability (mm) | Soiling resistance |
| --- | --- | --- |
| Example 1 | 0 | No coloration |
| Comparative Example 1 | 1.56 | Colored blackish gray |
| Example 2 | 0 | No coloration |
| Example 3 | 0 | No coloration |
| Example 4 | 0.2 | No coloration |

EXAMPLE 5 AND COMPARATIVE EXAMPLE 2

A molded article similar to that obtained in Example 1 was prepared in the same way as in Example 1 except that the polymerization temperature was changed to 65° C. and the polymerization time, to 5 hours.

A control molded article obtained in the same way as above except that DBS was not used contained a great amount of the unpolymerized material remaining there.

The amount of the remaining monomer and the surface hardness of the molded articles in Example 5 and Comparative Example 2 are shown in Table 2.

TABLE 2

| | Amount of the remaining monomer* | Surface hardness** |
| --- | --- | --- |
| Example 5 | None | 5H |
| Comparative Example 2 (control) | 48 ppm | H |

*The amount of the remaining monomer was determined by treating a sample having a volume of 10 dm$^2$ with a 20% aqueous solution of ethyl alcohol at 60° C., and measuring the amount of the monomer extracted in ethyl alcohol.
**The surface hardness is a pencil hardness which serves as a measure of completion of the polymerization.

What is claimed is:

1. An acrylic resin article consisting essentially of a methyl methacrylate polymer and dibenzylidene sorbitol or its derivative wherein the amount of dibenzylidene sorbitol or its derivative is from 0.1 to 3.0% by weight based on the total weight of the methyl methacrylate polymer and dibenzylidene sorbitol or its derivative.

2. The article of claim 1 wherein the dibenzylidene sorbitol derivative is a ring compound having an alkyl group or an alkoxy group substituted on the ring.

3. A process for producing an acrylic resin article, which comprises placing in a mold a composition comprising a methyl methacrylate monomer or a mixture of a methyl methacrylate polymer and a methyl methacrylate monomer and dibenzylidene sorbitol or its derivative, wherein the composition contains 0.1 to 3% by weight of dibenzylidene sorbitol or its derivative based on the total weight of the methyl methacrylate component and the dibenzylidene sorbitol component; and thereafter polymerizing the methyl methacrylate monomer in the composition.

4. The process of claim 3 wherein the polymerization is carried out at a temperature of 40° to 100° C.

* * * * *